United States Patent [19]

Hess

[11] Patent Number: 4,483,182

[45] Date of Patent: Nov. 20, 1984

[54] PENETRATION TEST KIT

[75] Inventor: Norman B. Hess, No. Salt Lake, Utah

[73] Assignee: Betz Laboratories, Inc., Trevose, Pa.

[21] Appl. No.: 348,116

[22] Filed: Feb. 11, 1982

[51] Int. Cl.³ .................... G01N 5/00; G01N 11/00
[52] U.S. Cl. ........................................ 73/73; 73/53
[58] Field of Search .............. 73/61.4, 73, 53, 432 Z

[56] References Cited

U.S. PATENT DOCUMENTS 2,217,175 8/1938 Ledbetter ............................. 73/73

FOREIGN PATENT DOCUMENTS 1166754 11/1958 France ................................. 73/61.4

Primary Examiner—Gerald Goldberg
Assistant Examiner—Hezron Williams
Attorney, Agent, or Firm—Alexander D. Ricci; Bruce E. Peacock

[57] ABSTRACT

An apparatus is provided to measure the wetting efficacy of certain dust control chemical additives. These additives are commonly sprayed on the dust to control and/or prevent the dissemination of the dust into the atmosphere. The device comprises a plurality of dust collection cylinders, each of which is adapted to retain a dust sample and the particular chemical additive for which testing is desired. A support is provided to support the cylinders and a visual display is operatively associated with the cylinders so as to indicate when the particular additive has completely penetrated the dust and thereby contacted the visual display.

2 Claims, 3 Drawing Figures

PENETRATION TEST KIT

FIELD OF THE INVENTION

The present invention relates to an apparatus for measuring the wetting efficacy of certain dust control chemical additives, which additives are adapted to control and/or prevent the dissemination of dust particles into the atmosphere.

BACKGROUND OF THE INVENTION

The presence of airborne particulate matter poses a serious hazard with respect to both the environment in general and personal health and safety in particular. For example, wind errosion of mine trailings has seriously disrupted normal living in the vicinity of certain mining localities. This dust contaminates food, potable water sources and fertile soils and, in some instances, interferes with the driving of automobiles on adjacent highways. In addition, airborne particles from any given source are often inhaled, resulting in serious respiratory ailments such as silicosis.

Common industrial sources of such dust has been categorized as open operations, leaks and spills, storage and disposal, and in completely controlled points and-/or housekeeping. The iron and steel industries are replete with examples of these enumerated categories. For example, steel mills have been ordered to install systems to control the dust, smoke, and sparks from electrical furnaces associated therewith. These particles emanated from what would best be categorized as the "open operations" noted above. The abovenoted disposal and storage source of dust is exemplified by the facts surrounding the use of the steel mill open hearth precipitator which has an electrostatic precipitator to control dust emissions. The dust removed by the electrostatic precipitator is typically collected in hoppers and periodically dumped in essentially closed containers known as "collecting". Despite the fact that connecting hoses are extended between the hopper and collecting fan, considerable dust emissions occur during material transfer. If the electrostatically removed particulate matter is to be used as landfill, several dust emissions can occur during the dumping and natural winds have been observed creating great dust clouds at the particular landfill site. The transportation of particulates along conveyor belts and the dumping of the particulates therefrom also create fugitive dust emission problems of the "transportation and disposal" source type. The "leaks and spills" and "poor housekeeping" sources of dust emissions are seen to be self-explanatory and, thus, further explanation of these categories is considered unwarranted.

In this light, certain chemical additives have been developed which are adapted to wet the troublesome dust, and to thereby control the dissemination thereof into the atmosphere. One such chemical compound is disclosed in U.S. Pat. No. 4,171,276 (Brehm)—of common assignment herewith.

Although the prior art located as a result of a preliminary examination directed toward this invention did not uncover any devices which are specifically adapted to the problem of measuring the wetting efficacy of dust control chemical additives, several of the located patents may be of interest. For instance, in U.S. Pat. No. 2,217,175 (Ledbetter) a method of testing drilling fluid is disclosed wherein mud is introduced into a ring member and the ring and mud are placed atop filter paper. The time required after the introduction of the mud into the ring for absorbed water to make its appearance at the outer edge of the filter paper is noted and used to evaluate formation penetration characteristics of the mud.

In U.S. Pat. No. 3,572,090 (Graham et al) an apparatus and method for testing the absorbancy characteristics of paperboard is disclosed. In accordance with the disclosed apparatus, a chamber is provided to contain a predetermined amount of liquid. Means for supplying liquid to the chamber are provided as well as are means for maintaining a sample of the paperboard to be tested with only a cut edge thereof exposed to the liquid in the chamber. Further, photoelectric means and a calibrated capillary tube are provided to measure the rate of which the predetermined amount of liquid changes as liquid is absorbed into the cut paperboard edge.

U.S. Pat. No. 3,952,584 (Lichstein) discloses a device for the measurement of absorbancy characteristics of absorbant structures. The disclosed device comprises a liquid reservoir having an opening at its bottom and a closed air-tight top. Further, a plate or the like is provided in communication with the sample to be tested. Liquid is drawn from the reservoir via capillary action, and the wetting rate of the sample is measured as the partial capacity or the volume of liquid absorbed as a function of time.

Other patents located during the preliminary search, which may be of interest, consist of U.S. Pat. No. 2,121,423 (Colbeth); U.S. Pat. No. 2,651,936 (Marnon et al); U.S. Pat. No. 3,067,622 (Ballestra) and U.S. Pat. No. 3,605,501 (Chenevert).

Despite the efforts of the prior art, there remains a need for a device which can measure the wetting efficacy of certain chemical additives which are adapted to wet and thereby control the dissemination of dust particles in the atmosphere. There is a more specific need in the art for such a device which is portable, and can be readily assembled at a test site, without need for any power source. There is a more specific need for such a device which is capable of measuring the wetting efficacies of a plurality of chemical additives, in simultaneous manner.

These and other objects are met by the invention described and claimed herein. The invention is herein described in detail in the following detailed description of the invention which should be read in conjunction with the appended drawings.

DRAWINGS

DETAILED DESCRIPTION OF THE INVENTION

Figure 1:
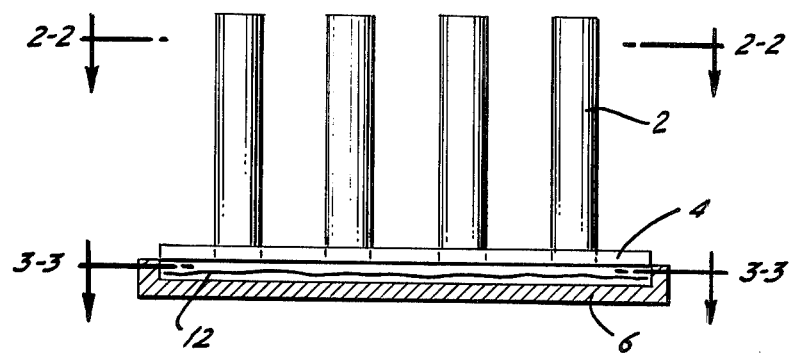
FIG. 1 is a side view of an apparatus in accordance with the invention.

With respect to FIG. 1, there is shown a device in accordance with the invention comprising a plurality of dust collection cylinders 2, each of which is adapted for retaining the particular dust sample and chemical additive for which wetting efficacy measurement is desired. The cylinders 2 are adjacently arranged in a row and are mounted in mounting means 4 which in turn is set atop support tray 6. It is noted that the cylinders 2 are completely open at the top and bottom end portions. Filter paper 12 is interposed between the bottom ends of the cyclinders 2 and the support tray 6. It is adapted to act as a visual display means to indicate to the user when the particular additive in a given cylinder 2 has completely penetrated the dust and thereby contacted the filter paper.

Figure 2:
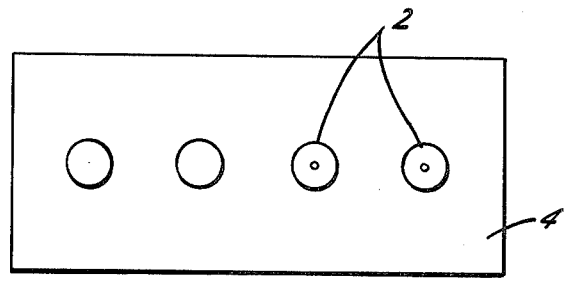
FIG. 2 is a sectional view taken along the plane 2—2 indicated by the lines and arrows 2—2 shown in FIG. 1.
Figure 3:
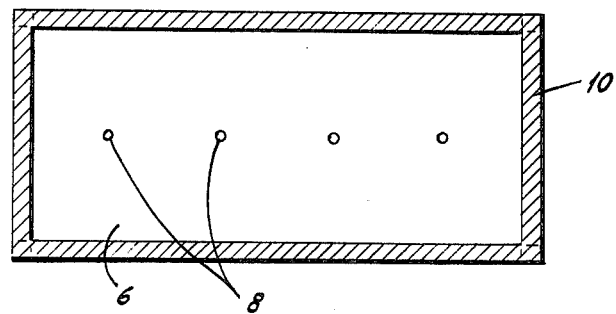
FIG. 3 is a sectional view taken along the plane 3—3 indicated by the lines and arrows 3—3 shown in FIG. 1.

With respect to FIGS. 1-3, it is seen that the tray 6 is provided with a plurality of notches 8 therein, which are arranged in a row across the tray. The cylinders 2 are to be positioned directly above these notches when the device is in operation.

The particular dust sample may first be crushed by means of a mortar and pistle if desired. The dust sample is then filled into each cylinder so that each cylinder is thereby about three-quarters full with the prepared particulate. The last quarter of the cylinder is then filled with the desired liquid to be tested. It may be desirable to fill one of the cylinders 2 with a control liquid such as water.

As soon as the liquid contacts the particulate mass disposed within the cylinders 2, the operator may begin timing the wetting operation via a stop watch or other means. The operator then simply records the time it takes until penetration of the dust has been made by the particular liquids; the penetration being signaled by means of the filter paper 12 becoming wet.

It thus becomes apparent that the operator may simultaneously test several different chemical additives or differing concentrations of the same additive along side each other, in order to gauge the relative wetting efficacies thereof.

The skilled artisan will readily appreciate that as the concentration of the dust control chemical additive in an aqueous or other carrier is increased, both absorption and penetration rates increase. Therefore, the device may be used to determine the particular concentration at which the dust control additives are to be used.

The device is especially well-suited to aid in the control of dust dissemination at conveyor belt transfer points. This control is a matter of timing. Prior to the time in which transfer occurs, the aqueous mixture comprising the dust control additive must be absorbed and must penetrate. To optimize chemical usage, the desired absorption and penetration should occur only moments before the transfer point.

Another application for the device may be found in the control of inventory pile type dust, which differs considerably from conveyor belt applications. For instance, timing is not near as critical. The concern is to obtain absorption. As long as this occurs before the water runs off the pile, it is considered adequate. The most important consideration in controlling dust from inventory piles is the depth of penetration. The best depth of penetration should be determined for each application.

While there has been described and pointed out the fundamental novel features of the invention as applied to the presently preferred embodiment, those skilled in the art will appreciate that various modifications, changes and omissions in the measuring device herein disclosed and described can be made without departing from the true spirit of the invention as defined in the amended claims.

I claim:

1. A portable apparatus for measuring the wetting efficacy of dust control chemical additives comprising a plurality of dust collection cylinders, each cylinder adapted to retain a dust sample and an additive or control additive, a single support means for supporting said cylinders, said dust collection cylinders being adjacently disposed atop said single support, and a common visual display means interposed between said support and said cylinders for indicating which said additive is the quickest to penetrate the dust and to thereby contact said visual display means.

2. Apparatus as recited in claim 1 wherein said command visual display means comprises filter paper.

* * * * *